(12) United States Patent
Bonassa (10) Patent No.: US 8,186,344 B2
(45) Date of Patent: May 29, 2012

(54) METHOD AND SYSTEM TO CONTROL MECHANICAL LUNG VENTILATION

(75) Inventor: Jorge Bonassa, Sao Paulo (BR)

(73) Assignee: Intermed-Equipamento Medico Hospitalar LTDA., Sao Paulo (BR)

( * ) Notice: Subject to any disclaimer, the term of this patent is extended or adjusted under 35 U.S.C. 154(b) by 815 days.

(21) Appl. No.: 12/264,122

(22) Filed: Nov. 3, 2008

(65) Prior Publication Data

US 2009/0114223 A1    May 7, 2009

(51) Int. Cl.
*F23D 11/00* (2006.01)
*F23D 14/00* (2006.01)

(52) U.S. Cl. ......... 128/203.26; 128/204.21; 128/204.23; 128/200.24; 128/204.18; 128/204.22; 600/529; 600/532

(58) Field of Classification Search ............. 128/204.21, 128/204.23, 203.26, 200.24, 204.18, 204.22
See application file for complete search history.

(56) References Cited

U.S. PATENT DOCUMENTS

| | | | | |
|---|---|---|---|---|
| 6,626,174 | B1* | 9/2003 | Genger et al. | 128/204.21 |
| 7,810,497 | B2* | 10/2010 | Pittman et al. | 128/204.23 |
| 2003/0010344 | A1* | 1/2003 | Bird | 128/205.24 |
| 2003/0078619 | A1* | 4/2003 | Bonnet et al. | 607/4 |
| 2003/0111079 | A1* | 6/2003 | Matthews et al. | 128/204.18 |
| 2006/0084877 | A1* | 4/2006 | Ujhazy et al. | 600/483 |

* cited by examiner

*Primary Examiner* — Loan Thanh
*Assistant Examiner* — Bradley Philips
(74) *Attorney, Agent, or Firm* — Fulbright & Jaworski L.L.P.

(57) ABSTRACT

The present disclosure refers to a system to control mechanical lung ventilation with volume band, more particularly a system to manage respiratory cycles in patients. Preferably, said respiratory cycles are controlled under pressure, so that the volumes as inspired by the patient are maintained within a volume range, comprising a lower volume limit and an upper volume limit, which are previously determined.

20 Claims, 5 Drawing Sheets

METHOD AND SYSTEM TO CONTROL MECHANICAL LUNG VENTILATION

CROSS-REFERENCE TO RELATED APPLICATIONS

This Application claims priority under 35 USC §119(a) to Brazilian Patent Application Number PI 0705091-7 filed on Nov. 1, 2007, which is incorporated by reference herein in its entirety.

BACKGROUND OF THE INVENTION

Patients requiring artificial ventilation are usually connected to lung ventilators administering in cycles, by means of positive pressure, tidal volumes of a mixture composed by air and oxygen. In an acute respiratory failure condition, the patient is usually sedated or in apnea state, i.e. there is no breathing effort and mechanical ventilation is made by means of controlled cycles.

Controlled cycles may usually be volume controlled or pressure controlled. Volume controlled cycles present a fixed flow pattern and any change in the respiratory mechanics results in change of the pressure in the patient's airway. Controlled pressure mode, on the other hand, keeps pressure in the patient's airway constant, presenting free demand flow and the volume is consequently variable.

When the patient shows any breathing effort, cycles may be synchronized with the patient's efforts and are then designated as assisted cycles. In case of assisted cycles, the controlled volume mode, despite being synchronized with the patient's initial effort, does not allow flow synchronization along the cycle, thus resulting in discomfort for the patient. On the other hand, the controlled pressure mode allows the patient to modulate the inspiratory flow, but does not ensure the resulting tidal volume is appropriate for proper respiratory support.

In one stage when the patient has better control over ventilation, spontaneous cycles may be made available through the ventilator. Usually, these cycles are partially assisted by the ventilator by means of a pressure support similar to the one used in the controlled pressure mode. Also in this case, the lack of control over the volume is a critical point, especially in patients at the initial phase of being weaned off ventilator support.

Clinical studies show the existence of a natural variability pattern in spontaneous or assisted breathing by patients, including newly born patients, and its potential beneficial effects. The variability of the respiratory pattern is linked e.g. to the success ventilator prosthesis weaning, besides a positive repercussion in respiratory mechanics and gas exchanges.

This variability pattern is practically suppressed by the use of the state of art ventilation modes, wherein, by means of various techniques, a pre-defined target volume is attempted to be reached and maintained.

Considering the above explanations, it is clear that there is a need to improve current ventilation modes, so to, at the same time, assure that safe ventilation limits are maintained and preserve the natural variability as present in patient's spontaneous breathing.

BRIEF SUMMARY OF THE INVENTION

The present disclosure refers in part to a method to control mechanical lung ventilation with volume band, more particularly a method using a system to safely manage respiratory cycles in patients. Preferably, said respiratory cycles are controlled under pressure, so that the volumes as inhaled by the patient are maintained within a volume range, comprising a lower volume limit and an upper volume limit, which are previously determined.

More specifically, the methods of the present disclosure generally comprises a ventilation system allowing inhaling volumes of respiratory cycles controlled under pressure to vary within a pre-established range, limiting maximum volume and/or increasing the pressure level so to keep volumes as received by the patient above a minimum volume. Therefore, the natural variability pattern as observed in human breathing is preserved, assuring at the same time the administration of volumes within pre-established limits.

An object of the present invention is therefore to provide in some embodiments a method and system of mechanical lung ventilation control solving inconveniences and/or improving artificial respiratory systems as known in the state of the art.

More particularly, an object of the present invention is to provide some embodiments comprising a lung ventilation control system to efficiently and safely control the volume delivered to the patients, keeping said volume within a volume range comprising pre-determined lower and upper limits.

Another object of the present invention is to provide some embodiments in which a system to control lung ventilation eliminates the risks of inhalation of an insufficient or excessive volume of air and oxygen by the patient during mechanical lung ventilation, consequently reducing the chances for secondary problems to patients due to compromise of their respiratory system.

Some aspects of the present invention may be ascertained by reference to the following consecutively numbered sentences, including material incorporated from other numbered sentences when so indicated:

1. METHOD TO CONTROL MECHANICAL LUNG VENTILATION, characterized by comprising a safe band of volume as defined by a lower volume limit and an upper volume limit and comprising the steps of:
    i) monitoring the volume as inspired by the patient during the respiratory cycles for the inspiratory time IT;
    ii) detection that the volume as inspired by the patient is outside limits as defined by the safe volume range, so that:
    a) if it detects that the inspired volume has reached the maximum limit, the flow and pressure valve is closed and the exhalation valve is opened;
    b) if it detects that the inspired volume is below the minimum lower limit:
    the number of cycles N below said minimum limit within a pre-determined time interval T is counted;
    N is compared to a reference value NR, as pre-defined or pre-adjusted by the operator, and, if N is equal to or higher than NR, the pressure value P increases to P+UP, being UP a pre-defined value;
    volume monitoring of cycles is re-started for a new time interval TC.

2. METHOD of sentence 1, characterized by being applied in controlled, assisted and/or spontaneous respiratory cycles.

3. METHOD of sentence 1, characterized by the pressure P being controlled pressure PC, support pressure PS and pressure rise UP is controlled or assisted pressure rise UPC and support pressure rise UPS.

4. METHOD of sentence 1, characterized by the exhalation valve only opening during step (a) after the end of the adjusted inspiratory time TI.

5. METHOD of sentence 1, characterized by the pressure rise value UP being established from the difference between the average volume of cycles out of the range and the average range value.

6. METHOD of sentence 1, characterized by the number of reference cycles NR being established from the analysis of statistical distribution of respiratory cycle volumes within a given period of time.

7. METHOD of sentence 6, characterized by the number of reference cycles NR being the number of cycles corresponding to the lower limit of normal distribution which deviation is higher than two standard deviations of the sample.

8. METHOD of sentence 6, characterized by the number of reference cycles NR corresponding to a percentage of the total respiratory frequency.

9. METHOD of sentence 1, characterized by the maximum pressure rise value by UP being limited by a limit pressure PL.

10. METHOD of sentence 1, characterized by the resulting pressure P+UP being retroactively adjusted until returning to the initially adjusted value P.

11. METHOD of sentence 10, characterized by the resulting pressure reduction P+UP being made by the following steps:
   i) counting of the number of cycles N2 within a second time interval T2, in which they present a volume below a second lower limit;
   ii) comparison between the number of cycles N2 and a second reference value NR2; if N2 is equal to or lower than NR2, the pressure value is reduced by a DP value.

12. METHOD of sentence 11, characterized by the pressure reduction DP being controlled or assisted pressure reduction DPC or the support pressure reduction DPS.

13. METHOD of sentence 11, characterized by the second lower volume limit being represented by the multiplication of the first lower limit by a factor K varying between 1.1 and 1.5.

14. METHOD of any of sentences 1 and 11, characterized by the pressure reduction value DP being equal to or lower than the pressure rise value UP.

15. METHOD of sentence 2, characterized by the following control parameters being defined in controlled and assisted respiratory cycles: Respiratory Frequency FR; Sensitivity S; Inhalation Time TI, Controlled Pressure PC, Minimum Controlled Value VCMin and Maximum Controlled Volume VCMax.

16. METHOD of sentence 2, characterized by the following control parameters being defined in spontaneous respiratory cycles: Support Pressure PS, Minimum Spontaneous Volume VSMin, Maximum Spontaneous Volume VSMax.

17. METHOD of sentence 2, characterized by also defining the Exhalation Pressure PEEP of the patient.

18. METHOD of sentence 2, characterized by the inspiratory flow F(t) and the inspired volume ∫F(t)·dt within the interval dt for pressure controlled cycles being given by:

$$PC-PEEP=F(t)\cdot R+\int F(t)\cdot dt/C$$

in which:
R: Resistance of airways
C: Compliance of the respiratory system.

19. METHOD of sentence 2, characterized by the inspiratory flow F(t) and the inspired volume ∫F(t)·dt within the interval dt for assisted cycles being given by:

$$PC+Effort-PEEP=F(t)\cdot R+\int F(t)\cdot dt/C$$

in which:
R: Resistance of airways
C: Compliance of the respiratory system
Effort: Inspiratory effort by the patient.

20. METHOD of sentence 2, characterized by the inspiratory flow F(t) and the inspired volume ∫F(t)·dt within the interval dt for spontaneous cycles being given by:

$$PS+Effort-PEEP=F(t)\cdot R+\int F(t)\cdot dt/C$$

in which:
R: Resistance of airways
C: Compliance of the respiratory system
Effort: Inspiratory effort by the patient.

21. SYSTEM TO CONTROL MECHANICAL LUNG VENTILATION comprising a flow and pressure control valve (3) connected to a source of gas (11), an inspiratory tube (7) connected to the patient (12) by means of a "Y" type connector (10) which is connected within an expiratory tube (9) interconnected to an exhalation valve (4), being also provided with a flow transducer (5) located downstream from the flow and pressure control valve (3) and pressure transducer (6), which send signals to a central control unit (2) provided with a control panel (1) to control flow and pressure (3) and exhalation (4) valves, characterized by comprising a safe volume band as defined by a lower limit volume and an upper limit volume, as per the method defined by any of sentences 1 to 20.

22. SYSTEM of sentence 21, characterized by the flow and pressure (3) and exhalation (4) control valves being servo controlled by microprocessor.

23. SYSTEM of sentence 22, characterized by the flow and pressure (3) and exhalation (4) control valves being activated by solenoids and/or pneumatics.

24. SYSTEM of sentence 22, characterized by the flow and pressure valve (3) function being performed by a compressor or turbine.

25. SYSTEM of sentence 22, characterized by the exhalation valve function being performed by a simple orifice in the patient's connection.

26. SYSTEM of sentence 21, characterized by the following control parameters being defined in said control panel (1) in controlled and assisted respiratory cycles: Respiratory Frequency FR; Sensitivity S; Inhalation Time TI, Controlled Pressure PC, Minimum Controlled Value VCMin and Maximum Controlled Volume VCMax.

27. SYSTEM of sentence 21, characterized by the following control parameters being defined in said control panel (1) in spontaneous respiratory cycles: Support Pressure PS, Minimum Spontaneous Volume VSMin, Maximum Spontaneous Volume VSMax.

28. SYSTEM of sentence 21, characterized by the Positive End Expiratory Pressure PEEP being additionally defined in the control panel (1).

29. SYSTEM of sentence 21, characterized by the inspiratory flow F(t) and the inspired volume ∫F(t)·dt within the interval dt for pressure controlled cycles being given by:

$$PC-PEEP=F(t)\cdot R+\int F(t)\cdot dt/C$$

in which:
R: Resistance of airways
C: Compliance of the respiratory system.

30. SYSTEM of sentence 21, characterized by the inspiratory flow F(t) and the inspired volume ∫F(t)·dt within the interval dt for assisted cycles being given by:

$$PC+Effort-PEEP=F(t)\cdot R+\int F(t)\cdot dt/C$$

in which:
R: Resistance of airways
C: Compliance of the respiratory system
Effort: Inspiratory effort by the patient.

31. SYSTEM of sentence 21, characterized by the inspiratory flow F(t) and the inspired volume ∫F(t)·dt within the interval dt for spontaneous cycles being given by:

$$PS + Effort - PEEP = F(t) \cdot R + \int F(t) \cdot dt / C$$

in which:
R: Resistance of airways
C: Compliance of the respiratory system
Effort: Inspiratory effort by the patient.

BRIEF DESCRIPTION OF THE SEVERAL VIEWS OF THE DRAWING

Therefore, to allow better understanding of the lung ventilation control system of the present invention, we will disclose in detail the attached figures representing.

DETAILED DESCRIPTION OF THE INVENTION

Figure 1:
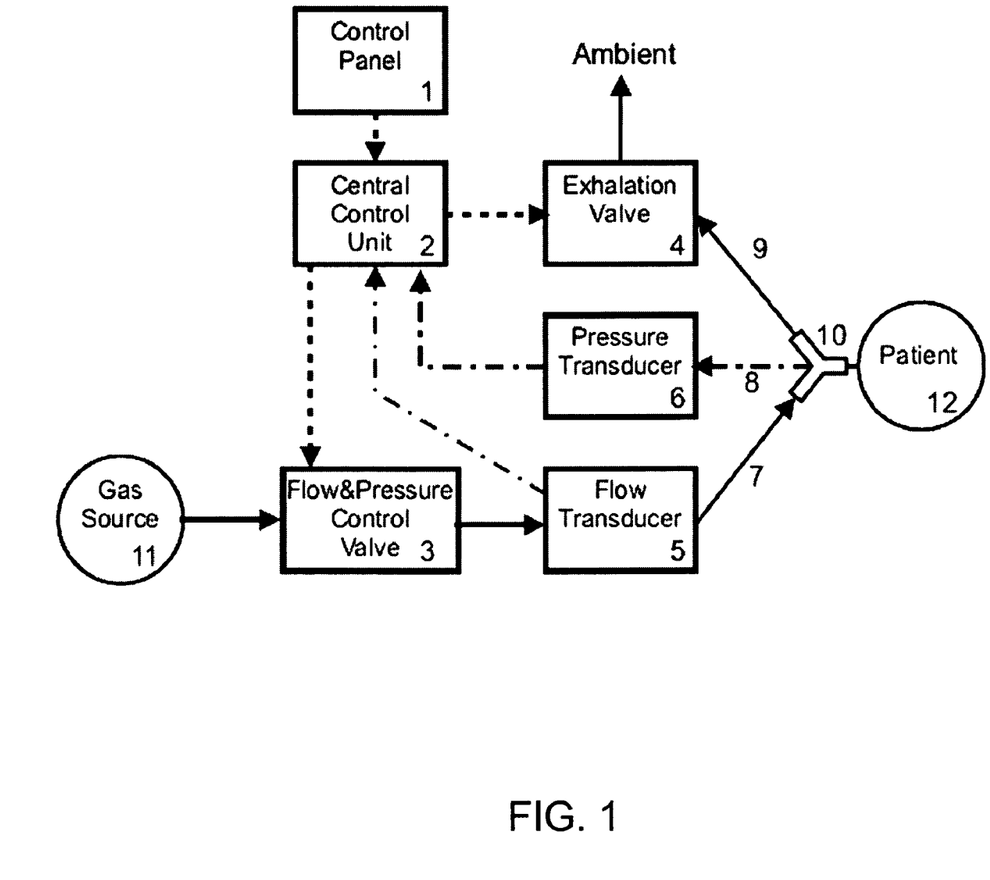
FIG. 1: schematic representation of a ventilator connected to the patient as per an embodiment of the present invention.

FIG. 1 schematically shows an embodiment of a ventilator system of the type as contemplated by the control system of the present invention, comprising a flow and pressure control valve 3 as connected to a source of gas 11, controlling the inspiratory flow by means of an inspiratory tube 7 connected to the patient 12 by means of a "Y" type connector 10. From the patient 12, the gas is exhaled through an exhalation tube 9 connected to the other end of the "Y" connector 10, according to the control of an exhalation valve 4. The pressure in the airway of the patient is sent from the "Y" connector 10 which is connected to a pressure transducer 6 through a tube 8.

The inspiratory flow is measured by the flow transducer 5 located downstream from the flow and pressure control valve 3. Both inspiratory flow and airway pressure signals, coming from flow transducer 5 and pressure transducer 6, jointly with parameters adjusted by the control panel 1, are used by the central control unit 2 to servo control flow and pressure control valve 3 and exhalation valve 4.

Flow and pressure control valve 3 and exhalation valve 4 are preferably servo controlled by a microprocessor, but may be activated by solenoids and/or pneumatics. Besides contemplating the typical configuration of a ventilation system, as detailed by FIG. 1, the present invention is not limited to this configuration, also contemplating other alternatives as commonly used, or even future alternatives which an expert in the art will know how to define in due time.

As examples, the present invention also encompasses embodiments wherein the flow and pressure control valve function is performed by a compressor or turbine; or an embodiment wherein the respiratory circuit has only one inspiratory branch and the function of the exhalation valve is performed by a simple orifice at the patient's connection; or an embodiment where the inspiratory and/or pressure flow are measured in different positions or even measured or estimated by different means.

The present invention encompasses embodiments of ventilation systems intended to invasive ventilation and ventilation systems intended to non-invasive ventilation, bearing in mind corrections as required to compensate the volume of gas which is lost e.g. in interfaces.

According to the objects of the present invention, some embodiments of the method of ventilation control comprise a system using a control unit receiving flow and pressure signals coming from respective transducers and controls exhalation and flow and pressure values.

In some embodiments, parameter values are adjusted to control respiratory cycles using a control panel. In a preferable configuration, the following control parameters are included:

Respiratory Frequency FR; Sensitivity S; Inspiratory Time TI; Controlled Pressure PC; Minimum Controlled Volume VCMin and Maximum Controlled Volume VCMax (controlled and assisted cycles); Support Pressure PS; Minimum Spontaneous Volume VEMin and Maximum Spontaneous Volume VEMax (spontaneous cycles). Other parameters may also be adjusted, such as Positive End Expiratory Pressure PEEP.

In particular embodiments, the method of the present invention comprises monitoring and controlling the mechanical lung ventilation system by establishing a safety range defining minimum and maximum volume limits to assure the correct supply of air and oxygen volumes, allowing natural breathing variability within safe limits as established.

In some embodiments, the method for mechanical lung ventilation control of the present invention comprises a safe range of volume as defined by a lower volume limit and an upper volume limit and comprises the steps of:

i) monitoring the volume as inspired by the patient during the respiratory cycles for the inspiratory time IT;

ii) detection that the volume as inspired by the patient is outside limits as defined by the safe volume range, so that:

a) if it detects that the inspired volume has reached the maximum limit, the flow and pressure valve is closed and the exhalation valve is opened;

b) if it detects that the inspired volume is below the minimum lower limit:

the number of cycles N below said minimum limit within a pre-determined time interval T is counted;

N is compared to a reference value NR, as pre-defined or pre-adjusted by the operator, and, if N is equal to or higher than NR, the pressure value P increases to P+UP, being UP a pre-defined value;

volume monitoring of cycles is re-started for a new time interval TC.

Examples below refer to cases in which the method and system of the present invention are applied under controlled respiratory cycles, be them assisted and/or spontaneous, but not being a limitation to the attached claims.

In cases in which the patient is in apnea state, i.e. with no inspiratory efforts, the ventilator will start controlled cycles according to the adjusted Respiratory Frequency FR. The equation establishing the inspiratory flow F(t) and the inspired volume ∫F(t)·dt within the interval between the start of the cycle t=t0 and the end of the cycle t=TI for pressure-controlled cycles is given below:

$$PC-PEEP = F(t) \cdot R + \int F(t) dt / C \quad (I)$$

in which:
R: Resistance of airways
C: Compliance of the respiratory system

As apparent from analyzing the equation (I), both the flow F(t) and the volume as obtained by the integral ∫F(t)·dt depend on both the adjusted parameters PC, PEEP and TI and the patient's respiratory mechanics as given by the resistance of airways R and the compliance of the respiratory system C.

The increase in resistance R or reduction of compliance C results in reduced flow and volume. On the other hand, a reduction of R or increase of C represents an increase of flow and volume.

Various clinical situations result in the change of respiratory mechanics, e.g. bronchial spasm and accumulation of secretions result in increased resistance; atelectasis and excessive respiratory insufficiency result in reduction of compliance; the administration of surfactant results in abrupt increase of compliance. Consequently, volume fluctuation when a ventilation mode in which pressure is the control variant is used, e.g. in modes with controlled pressure or support pressure, is a routine occurrence.

However, both volume reductions and increases above given levels represent risk to the patient. This problem is solved by applying embodiments of the methods herein establishing a safe volume range as defined by Maximum Volume VCMax and Controlled Minimum Volume VCMin.

Figure 2:
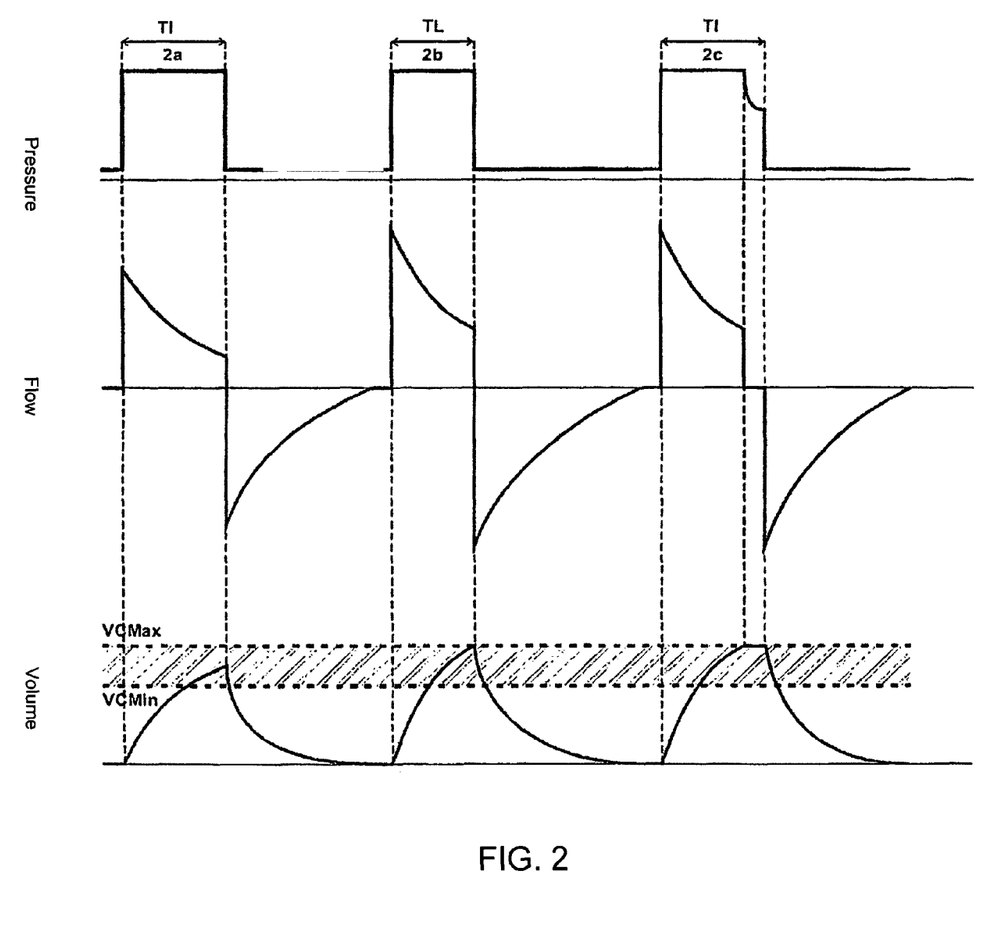
FIG. 2: representation of pressure, flow and volume curves of a hypothetical patient, showing controlled cycles with volume variations at the higher end of the safety band as per an embodiment of the control system object of the present invention.

FIG. 2 shows pressure, flow and volume curves of a hypothetical patient, representing cycles with volume variations at the higher end of the safety range. Curve 2a represents controlled cycle within the safety range. Curves 2b and 2c represent cycles which volumes have reached the upper limit of the range. In a preferred embodiment, as shown by the curve 2b, the control system limits the volume according to the adjusted value VCMax, ending the controlled cycle by closing the flow/pressure control valve and opening the exhalation valve.

In a preferred embodiment, as shown by the curve 2c, the control system interrupts the flow by closing the flow/pressure control valve and keeps the exhalation valve closed until the end of the adjusted inhalation time TI. Under this configuration, the lung remains pressurized with maximum volume, until the end of the adjusted inspiratory time.

In both configurations, the volume of no cycle will be higher than the established maximum value, thus avoiding the risk of barotrauma.

Figure 3:
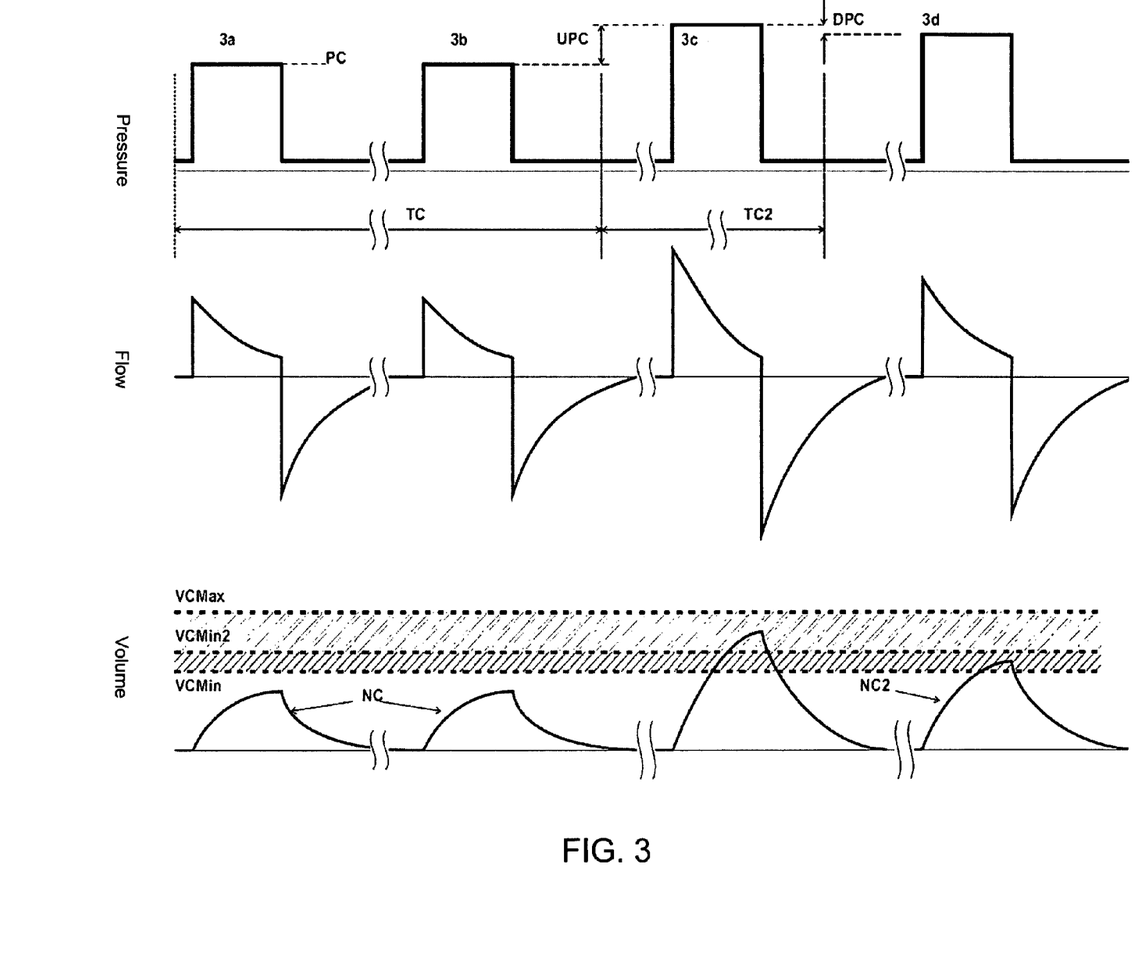
FIG. 3: representation of pressure, flow and volume curves of a hypothetical patient, showing controlled cycles with volume variations at the lower end of the safety band as per an embodiment of the control system object of the present invention.

FIG. 3 shows pressure, flow and volume curves of a hypothetical patient, representing cycles with volume variations at the lower end of the safety range, in a two-minute time interval.

As we can see from the trace of FIG. 3, a few cycles, represented by curves 3a and 3b, show lower volumes than the minimum value of the range VCMin. In a preferred embodiment, the control system counts within a pre-determined time interval TC the number of cycles NC1 presenting volumes below the lower limit of the range VCMin and compares it with a reference value NCR which is pre-defined or pre-adjusted by the operator. If NC1 is equal to or higher than NCR, the control system increases the controlled pressure value PC to PC+UPC, as shown by FIG. 3c.

In a preferred embodiment, TC value was established as one minute, the number of cycles NCR as 2 and the UPC value at 5 cm $H_2O$. In an alternative embodiment, UPC value may be established from the difference between the average volume of cycles out of the range and the average range value. In addition, alternatively, the number of cycles NCR may be established from the analysis of statistical distribution of the volumes of respiratory cycles within a given period. NCR value may correspond e.g. to the number of cycles corresponding to the lower limit of normal distribution which deviation is higher e.g. than two standard deviations of the sample. In another alternative embodiment, NCR may be a percentage of the total respiratory frequency.

From the elevation of controlled pressure to the PC+UPC value, monitoring of cycle volumes starts again for a new time interval TC.

If the condition of violation of the lower limit VCMin persists, UPC controlled pressure rises again and so successively, until the end of the violation.

In a preferred embodiment, the maximum value for controlled pressure increase is limited by an adjustable limit pressure value PL.

Whenever the effective value of controlled pressure is above the programmed value PC, the control system will attempt to reduce that value until the pressure returns to the originally programmed value, not reducing it below that value.

In a preferred embodiment, the control system counts within a pre-determined time interval TC2 the number of cycles NC2 presenting volumes below a second lower limit VCMin2, represented by the lower limit VCMin multiplied by factor KC, preferably 1.1<KC<1.5, pre-defined or pre-adjusted by the operator, and compares it with a reference value NCR2 which is pre-defined or pre-adjusted by the operator. If NC2 is equal to or lower than NCR2, the control system reduces the actual controlled pressure value e.g. considering that the pressure is (PC+UPC) to (PC+UPC)−DPC, preferably DPC≦UPC, as shown by FIG. 3d.

This preferred embodiment defines a second lower limit so to determine a second safety range within previously defined limits. More particularly, said embodiment allows the system to use the lower possible pressure values, above the programmed value, so to keep the volume of respiratory cycles above the established lower limit.

In a preferred embodiment, TC2 value was established as two minutes, factor KC=1.2, the number of cycles NCR2 as 2 and the DPC value at 2 cm $H_2O$. For the determination of DPC and NCR2, the same alternative means as previously disclosed for UPC and NCR may also be used. If the condition of violation of the lower limit VCMin2 persists, DPC controlled pressure is lowered again and so successively, until the end of the violation or until reaching the controlled pressure value as originally adjusted PC.

In case the patient shows inspiratory effort, depending on the mode of ventilation, assisted and/or spontaneous cycles will be initiated. Assisted cycles are usually controlled by the controlled pressure PC, while spontaneous cycles are controlled by the support pressure PS.

In this configuration of the present invention, the same controls as applied to controlled cycles are applied to assisted cycles, as previously disclosed. The distinction between cycles is made by the start-assisted cycles being initiated by the patient by adjusting the sensitivity control S, and controlled cycles are initiated by the ventilator so to sum up the programmed respiratory frequency FR. Furthermore, as a function of the existence of inspiratory effort from the patient, flow and volume vary as a function of the effort itself, besides the effects of respiratory mechanics, as we may verify from equation (II) below.

$$PC+\mathit{Effort}-PEEP=F(t)\cdot R+\int F(t)dt/C \qquad (II)$$

In which:
R: Resistance of airways
C: Compliance of the respiratory system
Effort: Inspiratory effort by the patient.

In case of spontaneous cycles, pressure controls are made available by the ventilator as independent from controlled and assisted cycles. For spontaneous cycles, we usually designate as support pressure PS the pressure control as applied. Besides being initiated by the patient, according to the sensitivity control S, spontaneous cycles are also finalized so to follow the inhalation effort by the patient. This is obtained by ending the respiratory cycle when the flow F(t) reaches a percentage of the peak of flow, usually reached at the start of the cycle, being said percentage pre-defined or adjusted by the operator. During spontaneous cycles, volume variations are higher as a function of better inspiratory control from the patient, according to equation (III) below:

$$PS+\mathit{Effort}-PEEP=F(t)\cdot R+\int F(t)dt/C \qquad (III)$$

In which:
R: Resistance of airways
C: Compliance of the respiratory system
Effort: Inspiratory effort by the patient.

However, for control purposes, the same means as previously disclosed for controlled and assisted cycles are applied, bearing in mind the use of different values to adjust pressure levels and the limits establishing the volume range: Support Pressure PS, Minimum Spontaneous Volume VSMin, Maximum Spontaneous Volume VSMax.

Analogously to the disclosure of the control system embodiments for controlled and assisted cycles, we include below the description as applied to spontaneous cycles.

Figure 4:
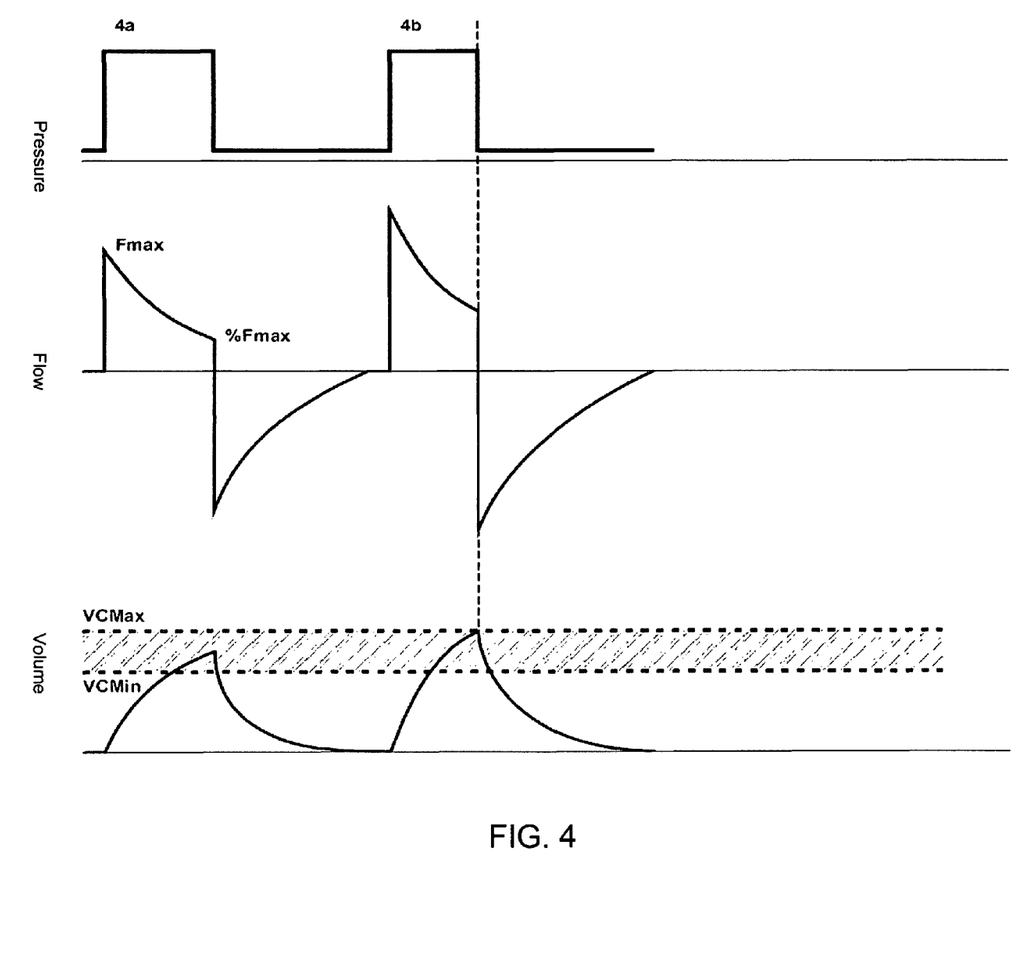
FIG. 4: representation of pressure, flow and volume curves of a hypothetical patient, showing spontaneous cycles with volume variations at the higher end of the safety band as per an embodiment of the control system object of the present invention.

FIG. 4 shows pressure, flow and volume curves of a hypothetical patient, representing spontaneous cycles with volume variations at the higher end of the safety range. Curve 4a represents a spontaneous cycle within the safety range. Curve 4b shows a cycle which volume reached the upper limit of the range VSMax. In a preferred embodiment, as shown by the curve 4b, the control system limits the volume according to the adjusted value VSMax, ending the controlled cycle by closing the flow/pressure control valve and opening the exhalation valve.

Figure 5:
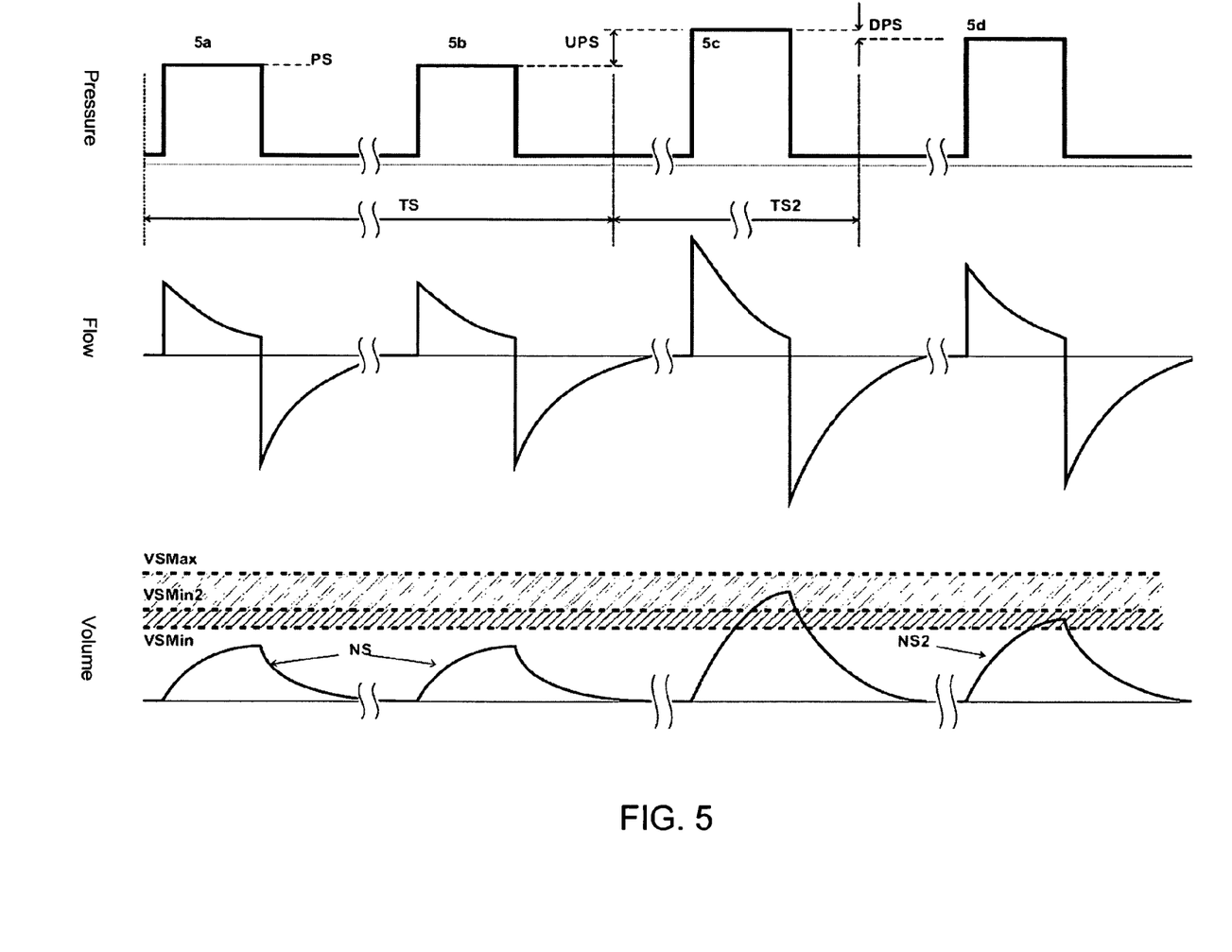
FIG. 5: representation of pressure, flow and volume curves of a hypothetical patient, showing spontaneous cycles with volume variations at the lower end of the safety band as per an embodiment of the control system object of the present invention.

FIG. 5 shows pressure, flow and volume curves of a hypothetical patient, representing spontaneous cycles with volume variations at the lower end of the safety range, in a two-minute time interval.

As we can see from the trace of FIG. 5, a few cycles, represented by curves 5a and 5b, show lower volumes than the minimum value of the range VSMin. In a preferred embodiment, the control system counts within a pre-determined time interval TS the number of cycles NS1 presenting volumes below the lower limit of the range VSMin and compares it with a reference value NSR which is pre-defined or pre-adjusted by the operator. If NS1 is equal to or higher than NSR, the control system increases the support pressure value PS to PS+UPS, as shown by FIG. 5c.

In a preferred embodiment, TS value was established as one minute, the number of cycles NSR as 2 and the UPS value at 5 cm $H_2O$. In an alternative embodiment, UPS value may be established from the difference between the average volume of spontaneous cycles out of the range and the average range value. In another alternative embodiment, the number of cycles NSR may be established from the analysis of statistical distribution of the volumes of respiratory cycles within a given period. NSR value may correspond e.g. to the number of cycles corresponding to the lower limit of normal distribution which deviation is higher e.g. than two standard deviations of the sample. In another alternative embodiment, NSR may be a percentage of the total respiratory frequency.

From the elevation of support pressure to the PS+UPS value, monitoring of cycle volumes starts again for a new time interval TS.

If the condition of violation of the lower limit VSMin persists, UPS controlled pressure rises again and so successively, until the end of the violation.

In a preferred embodiment, the maximum value for support pressure rise is limited by an adjustable limit pressure value PL.

Whenever the effective value of support pressure is above the programmed value PS, the control system will attempt to reduce the pressure up to the originally programmed value PS.

In a preferred embodiment, the control system counts within a pre-determined time interval TS2 the number of cycles NS2 presenting volumes below a second lower limit VSMin2, represented by the lower limit VSMin multiplied by factor KS, preferably 1.1<KS<1.5, pre-defined or pre-adjusted by the operator, and compares it with a reference value NSR2 which is pre-defined or pre-adjusted by the operator. If NS2 is equal to or lower than NSR2, the control system reduces the actual controlled pressure value e.g. considering that the pressure is (PS+UPS) to (PS+UPS)−DPS, preferably DPS≦UPS, as shown by FIG. 5d.

In a preferred embodiment, TS2 value was established as two minutes, factor KS=1.2, the number of cycles NSR2 as 2 and the DPS value at 2 cm $H_2O$. For the determination of DPS and NSR2, the same alternative means as previously disclosed for UPS and NSR may also be used.

If the condition of violation of the lower limit VSMin2 persists, DPS controlled pressure is lowered again and so successively, until the end of the violation or until reaching the controlled pressure value as originally adjusted PS.

All publications cited herein are incorporated by reference in their entireties and for the specific material referenced or relied upon herein, including the following:

1. U.S. Pat. No. 5,582,163
2. U.S. Pat. No. 6,679,258
3. U.S. Pat. No. 7,011,091
4. U.S. Pat. No. 5,647,350
5. Jaber S, Delay J M, Matecki S, Sebbane M, Eledjam J J, Brochard L., Volume-guaranteed pressure-support ventilation facing acute changes in ventilatory demand, *Intensive Care Med.* 2005 September; 31(9):1181-8. Epub 2005 Jul. 20.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

The invention claimed is:

1. A method to control mechanical lung ventilation, comprising a safe band of volume as defined by a first lower volume limit and a first upper volume limit and comprising the steps of:
   i) monitoring a volume as inspired by a patient during a respiratory cycle for an inspiratory time,
   ii) detecting when the volume as inspired by the patient is outside the first limits defining the safe volume range, by:
      a) determining whether an inspired volume has reached the first upper volume limit, such that a flow and/or a pressure control valve is closed and an exhalation valve is opened, and
      b) if the inspired volume is below the first lower limit:
         b1) at least one of a number of cycles below said first lower limit within a pre-determined time interval is counted;
         b2) the number of cycles below said first lower limit counted in step b1) is compared to a pre-defined or pre-adjusted reference value,
         b3) determining whether the number of cycles below said first lower limit counted in step b1) is equal to or higher than the pre-defined or pre-adjusted reference value, a pressure value is increased by a pre-defined pressure increase value, and
         b4) steps b1)-b3) are repeated until the number of cycles below said first lower limit counted in step b1) is less than the pre-defined or pre-adjusted reference value.

2. The method of claim 1, characterized by being applied in controlled, respiratory cycles.

3. The method of claim 1, wherein a) the pressure is a controlled pressure and/or support pressure and b) the pressure increase of b3) is a controlled and/or assisted pressure increase and/or support pressure increase.

4. The method of claim 1, wherein the exhalation valve only opens during step a) after an end of an adjusted inspiratory time.

5. The method of claim 1, wherein the pressure increase value of b3) is established from a difference between an average volume inspired in cycles where the volume is outside of the safe band of volume and an average range value.

6. The method of claim 1, wherein the pre-defined or pre-adjusted reference value is established from an analysis of a statistical distribution of a number of respiratory cycle volumes within a given period of time.

7. The method of claim 6, wherein the pre-defined or pre-adjusted reference value is a number of respiratory cycles corresponding to the lower limit of a normal distribution in which a deviation is higher than two standard deviations of a sample.

8. The method of claim 6, wherein the pre-defined or pre-adjusted reference value corresponds to a percentage of the total respiratory frequency.

9. The method of claim 1, wherein a total pressure increase value of ii), b) is limited by a limit pressure.

10. The method of claim 1, wherein the resulting increased pressure value of ii), b) is retroactively adjusted until returning to the initial pressure value.

11. The method of claim 10, wherein the resulting pressure reduction is made by the following steps:
    i) counting of the number of cycles within a second time interval, in which an inspiratory volume is below a second lower volume limit,
    ii) comparing the number of cycles counted in i) and a second predefined and/or pre-determined reference value, and
    iii) if number of cycles counted in i) is equal to or lower than the second pre-defined and/or pre-determined reference value, the pressure value is reduced by a pre-defined pressure decrease value.

12. The method of claim 11, wherein the pressure reduction is a controlled or an assisted pressure reduction or a support pressure reduction.

13. The method of claim 11, wherein the second lower volume limit is represented by the multiplication of the first lower volume limit by a factor K varying between 1.1 and 1.5.

14. The method of claim 11, wherein the pressure reduction value is equal to or lower than the pressure rise value.

15. The method of claim 2, wherein the following control parameters is defined in controlled and assisted respiratory cycles: Respiratory Frequency FR; Sensitivity S; Inhalation Time TI, Controlled Pressure PC, Minimum Controlled Value VCMin and Maximum Controlled Volume VCMax.

16. The method of claim 2, wherein the following control parameters is defined in spontaneous respiratory cycles: Support Pressure, Minimum Spontaneous Volume, Maximum Spontaneous Volume.

17. The method of claim 2, characterized by also defining the Exhalation Pressure of the patient.

18. The method of claim 2, wherein the inspiratory flow $F(t)$ and the inspired volume $\int F(t)\,dt$ within the interval $dt$ for pressure controlled cycles being given by:

$$PC-PEEP=F(t)\cdot R+\int F(t)dt/C$$

in which:
R: Resistance of airways
C: Compliance of the respiratory system.

19. The method of claim 2, wherein the inspiratory flow $F(t)$ and the inspired volume $\int F(t)dt$ within the interval $dt$ for assisted cycles is given by:

$$PC+Effort-PEEP=F(t)\cdot R+\int F(t)dt/C$$

in which:
R: Resistance of airways
C: Compliance of the respiratory system
Effort: Inspiratory effort by the patient.

20. The method of claim 2, wherein the inspiratory flow $F(t)$ and the inspired volume $\int F(t)dt$ within the interval $dt$ for spontaneous cycles is given by:

$$PS+Effort-PEEP=F(t)\cdot R+\int F(t)dt/C$$

in which:
R: Resistance of airways
C: Compliance of the respiratory system
Effort: Inspiratory effort by the patient.

* * * * *